(12) United States Patent
Gilad

(10) Patent No.: US 7,967,745 B2
(45) Date of Patent: Jun. 28, 2011

(54) IN VIVO IMAGING DEVICE AND METHOD OF MANUFACTURE THEREOF

(75) Inventor: Zvika Gilad, Haifa (IL)

(73) Assignee: Given Imaging, Ltd., Yoqneam (IL)

( * ) Notice: Subject to any disclaimer, the term of this patent is extended or adjusted under 35 U.S.C. 154(b) by 1303 days.

(21) Appl. No.: 11/528,628

(22) Filed: Sep. 28, 2006

(65) Prior Publication Data
US 2008/0081949 A1   Apr. 3, 2008

(51) Int. Cl.
*A61B 1/06* (2006.01)

(52) U.S. Cl. ........ 600/160; 600/109; 600/130; 600/920; 348/76

(58) Field of Classification Search ............ 600/109, 600/130, 160, 178, 179, 302, 920; 128/899; 348/76; 439/55, 586, 591, 754, 759, 761, 439/775, 786, 816, 830, 865, 867, 869, 871, 439/872
See application file for complete search history.

(56) References Cited

U.S. PATENT DOCUMENTS

| | | | |
|---|---|---|---|
| 4,025,162 A * | 5/1977 | Yagi ............................... 349/58 |
| 4,278,077 A | 7/1981 | Mizumoto |
| 5,604,531 A | 2/1997 | Iddan et al. |
| 5,993,378 A | 11/1999 | Lemelson |
| 5,999,414 A * | 12/1999 | Baker et al. ..................... 361/789 |
| 6,240,312 B1 | 5/2001 | Alfano et al. |
| 6,951,536 B2 * | 10/2005 | Yokoi et al. ..................... 600/128 |
| 7,009,634 B2 | 3/2006 | Iddan et al. |
| 7,731,510 B2 * | 6/2010 | Tada et al. ......................... 439/91 |
| 2002/0103417 A1 | 8/2002 | Gazdzinski |
| 2002/0109774 A1 | 8/2002 | Meron et al. |
| 2002/0111544 A1 | 8/2002 | Iddan et al. |
| 2003/0073935 A1 * | 4/2003 | Segawa et al. ................. 600/593 |
| 2003/0171652 A1 * | 9/2003 | Yokoi et al. ..................... 600/160 |
| 2004/0171914 A1 | 9/2004 | Avni |
| 2005/0171398 A1 * | 8/2005 | Khait et al. ..................... 600/102 |
| 2005/0179805 A1 * | 8/2005 | Avron et al. ................... 348/340 |
| 2006/0004257 A1 | 1/2006 | Gilad et al. |
| 2006/0015013 A1 | 1/2006 | Gilad et al. |
| 2006/0044614 A1 | 3/2006 | Cohen |
| 2010/0055996 A1 * | 3/2010 | Szu ................................ 439/852 |
| 2010/0124857 A1 * | 5/2010 | Kawamura et al. ........... 439/816 |

FOREIGN PATENT DOCUMENTS

| | | |
|---|---|---|
| DE | 3440177 A1 | 5/1986 |
| JP | 57-45833 | 3/1982 |
| JP | 4-109927 | 4/1992 |
| JP | 1992-144533 | 5/1992 |
| WO | WO 2004059568 A1 * | 7/2004 |

* cited by examiner

*Primary Examiner* — John P Leubecker
*Assistant Examiner* — Jeffrey H Chang
(74) *Attorney, Agent, or Firm* — Pearl Cohen Zedek Latzer, LLP

(57) ABSTRACT

The present invention provides, according to some embodiments, an in vivo imaging device, comprising a mount having at least one illumination source. The mount may be in electrical communication with the illumination source. The device may further include a circuit board and a contact clip for securing the mount to the circuit board and for providing electrical communication therebetween.

6 Claims, 4 Drawing Sheets

IN VIVO IMAGING DEVICE AND METHOD OF MANUFACTURE THEREOF

FIELD OF THE INVENTION

The present invention relates to an in vivo device, such as an imaging device, and a method for manufacture thereof.

BACKGROUND OF THE INVENTION

In-vivo devices, such as, for example, capsules, may be capable of gathering information regarding a body lumen while inside the body lumen. Such information may be, for example, a stream of data or image frames from the body lumen and/or measurements of parameters that are medically useful, such as, for example, pH. A sensing device may transmit the gathered information via a hard-wired or wireless medium, and the gathered information may be received by a receiver/recorder. The recorded information may be sent from the receiver/recorder to a workstation to be analyzed and/or displayed.

Such a system may be operated by, for example, health care professionals and technicians, in a hospital, or another health facility.

In some ingestible devices the electronic components within the device may be arranged on several boards, each board containing different components of the device. The image sensor, for example a silicon chip, may be positioned on one board whereas a transmitter for transmitting images may be positioned on a separate printed circuit board (PCB).

In some cases the different components must be aligned so that certain parts are positioned at specific angles for optimal operation to be achieved.

SUMMARY OF THE INVENTION

The present invention provides, according to some embodiments, an in vivo imaging device, comprising a mount having at least one illumination source. The mount may be in electrical communication with the illumination source. The device may further include a circuit board and a contact clip for securing the mount to the circuit board and for providing electrical communication therebetween.

According to one embodiment the mount may include a plurality of illumination sources, for example, light emitting diodes (LEDs). In one embodiment, the plurality of illumination sources may be arranged, for example, on a circuit board in a ring, and the mount may be referred to as an LED ring. Another embodiment may include an optical imager and the optical imager may be central to the ring. According to another embodiment the circuit board may further include a flexible portion extending from the circuit board with a second circuit board attached to the flexible extension. A second mount having a second plurality of illumination sources, for example, light emitting diodes (LEDs), arranged in a second ring and a second optical imager central to the second ring, and a second contact clip for securing the second mount to the second circuit board and securing the second mount to the base of a lens holder and to the circuit board for securing components of the imaging device and/or for providing electrical communication therebetween. According to still another embodiment of the present invention, a plurality of contact clips for securing the respective mounts to the respective circuit boards may be provided and a solder connection for enhancing the electrical communication provided by the contact clips.

According to yet another embodiment of the present invention, a method for manufacturing the plurality of embodiments of the disclosed in vivo imaging device is disclosed.

Optionally, the in vivo imaging device may include at least an image sensor and an illumination source. According to another embodiment the device may also include a transmitter for transmitting signals from a sensor, such as an image sensor, to a receiving system.

According to an embodiment, the circuit board may be folded and arranged in a stacked vertical fashion.

In another embodiment different components of the system may be attached on the circuit board and may be folded as necessary.

In another embodiment the circuit board may be capable of folding according to several designs, enabling the circuit board to fit into devices of different shapes and/or sizes.

Additionally, the device and method of some embodiments of the present invention may enable easy access to key components of the device even after their assembly and incorporation into the system.

Additionally, the device and method of some embodiments of the present invention may enable exact and meticulous assembly, finish and performance while keeping maintenance and costs of the parts at a minimum.

Additionally, embodiments of the present invention may enable assembly of parts to create a variety of shapes.

Additionally, the device according to embodiments of the present invention may be lightweight and flexible, enabling quick transformation and adjustment of shape and function according to the specific needs and requirement of the procedure performed.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1:
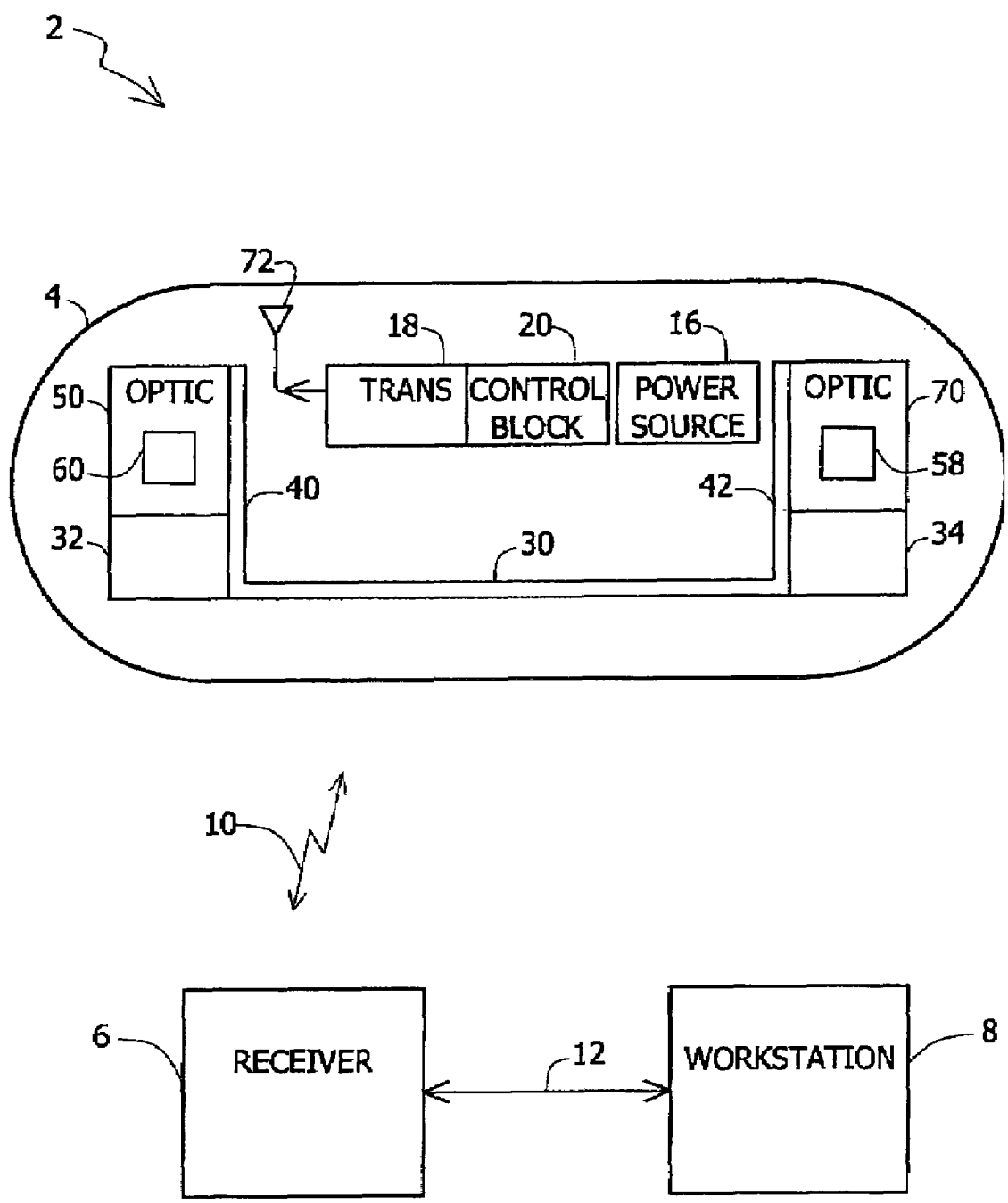
FIG. 1 is a simplified illustration of an exemplary in-vivo imaging system, including an in-vivo imaging device, a receiving unit, and a workstation, in accordance with an embodiment of the invention.

It should be noted that for simplicity and clarity of illustration, elements shown in the figures have not necessarily been drawn to scale. For example, the dimensions of some of the elements may be exaggerated relative to other elements for clarity. Furthermore, where considered appropriate, reference numerals may be repeated among the figures to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Some embodiments of the present invention are directed to a typically swallowable in-vivo device that may be used for recording and transmitting in vivo data, such as, for example, from the entire length of the gastrointestinal (GI) tract, to a receiving and/or processing unit. Other embodiments need not be swallowable or autonomous, and may have other shapes or configurations. For example, the present invention may be practiced using an endoscope, needle, stent, catheter, etc. Some in-vivo devices may be capsule shaped, or may have other shapes, for example, a peanut shape or tubular, spherical, conical, or other suitable shapes. According to some embodiments the in vivo device may include an image sensor, however, other sensors may be used.

Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. Pat. No. 7,009,634 to Iddan et al., entitled "Device for In-Vivo Imaging", and/or in U.S. patent application Ser. No. 10/046,541, entitled "System and Method for Wide Field Imaging of Body Lumens", filed on Jan. 16, 2002, published on Aug. 15, 2002 as United States Patent Application Publication No. 2002/0109774, and/or in U.S. patent application Ser. No. 10/046,540, entitled "System and Method for Determining In-vivo Body Lumen Conditions", filed on Jan. 16, 2002, published on Aug. 15, 2002 as United States Patent Application Publication No. 2002/0111544, all of which are hereby incorporated by reference in their entirety.

Reference is made to FIG. 1, which is a simplified illustration of an exemplary in-vivo imaging system 2, including an in-vivo imaging device 4, a receiving unit 6, and a workstation 8, in accordance with an embodiment of the invention.

Workstation 8 may include a display unit, a processor, and a memory. Workstation 8 may accept, process and/or display image data received from receiving unit 6.

Receiving unit 6 may include an antenna, a transmitter, a transceiver, a processor, a memory, and a power source. The processor may control, at least in part, the operations of receiving unit 6. According to some embodiments of the invention, imaging device 4 may be a capsule, although other configurations are possible. In some embodiments having receiving unit 6 separate from workstation 8 need not be used. Any unit which may receive or accept data transmitted by imaging device 4 may be considered a "receiving unit".

Receiving unit 6 may communicate with workstation 8 via a medium 12, which may be wireless or hard-wired. For example, receiving unit 6 may be able to transfer bits of wireless communication, for example, memory data or corresponding image frames that are stored in memory to workstation 8, and may receive control signals, and other digital content, from workstation 8. Although the invention is not limited in this respect, medium 12 may be, for example, a USB cable and may be coupled to a USB controller in receiving unit 6. Alternatively, medium 12 may be wireless, and receiving unit 6 and workstation 8 may communicate wirelessly.

Figure 2:
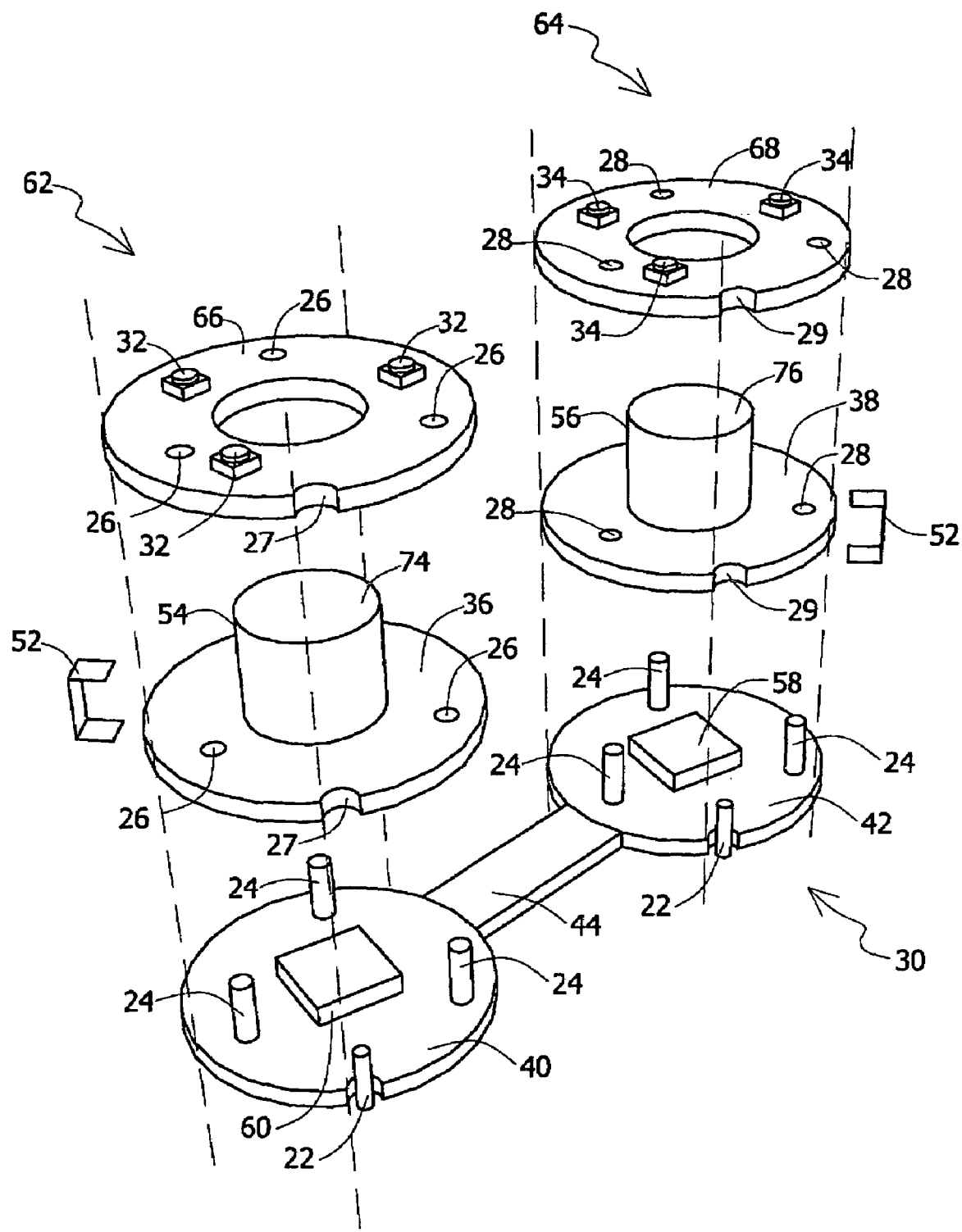
FIG. 2 is a schematic illustration showing mounts, bases, and a circuit board, according to an embodiment of the invention.

Imaging device 4 may include a power source 16, a transmitter 18, an antenna 72, a control block 20, optical systems 50 and 70, illumination sources 32 and 34, for example, arranged in a ring (as shown in FIG. 2), and a circuit board 30. Power source 16 may electrically connected to electrical components, for example, transmitter 18, control block 20, optical systems 50 and 70, illumination sources 32 and 34, and circuit board 30. Transmitter 18 may include, for example, a transmitter module or sub-unit and a receiver module or sub-unit, or an integrated transceiver or transmitter-receiver. Any unit or sub-unit which may transmit or send data, for example, from imaging device 4 may be considered a "transmitter". Optical systems 50 and/or 70 may include imaging sensors 60 and 58, optical windows 74 and 76 (shown in FIG. 2), lenses, and lens holders 54 and 56 (shown in FIG. 2), respectively. Image sensors 60 and 58 may provide images to transmitter 18 for transmitting, for example, via antenna 72. Illumination sources 32 and 34 may produce light pulses that may penetrate through optical windows 74 and 76 and may illuminate inner portions of a body lumen, which may be imaged, for example by optical imagers 60 and 58, respectively. Illumination sources 32 and 34 may include for example white LEDs and one or more resistors. Illumination sources 32 and 34 may be positioned on opposite ends of imaging device 4.

Image data collected by image sensors 60 and/or 58, may be transmitted, for example, via transmitter 18, from imaging device 4 to receiving unit 6 via a wireless or hard-wired medium 10. It may be appreciated by those skilled in the art that, with appropriate modifications, any number of imaging systems may be used according to embodiments of the invention.

Control block 20 may control, at least in part, the operations of imaging device 4. For example, control block 20 may synchronize time periods, in which illumination sources 32 and 34 produce light rays or pulses with time periods in which optical imagers 60 and 58 capture images, respectively.

In various embodiments, circuit board 30 may be flexible, moveable, jointed, rigid and/or rigid-flex and may be assembled or configured for insertion into imaging device 4. For example, circuit board 30 may be a one sheet flexible circuit board, for example, a printed circuit board (PCB) made of, for example, silicone or plastic. Other suitable materials or shapes may be used. Circuit board 30 may be packaged in its spread out form before it is inserted into imaging device 4. According to one embodiment, circuit board 30, in its spread out form, may have a length equal to or less than about 36.5 mm (measured along a centerline of circuit board 30) and a breadth less than or more than about 13 mm (measured between the edges either of portions 40 and 42). Circuit board 30 may be suitable for use in imaging device 4, which is about 20-30 mm long. Flexible circuit boards and micro technology according to embodiments of the invention may be similar to flexible boards produced by Al-tech of Petach-Tikva, Israel. Other dimensions or sizes may be used.

Imaging device 4 typically may be or may include an autonomous swallowable capsule, but imaging device 4 may have other shapes and need not be swallowable or autonomous. Embodiments of imaging device 4 are typically autonomous, and are typically self-contained. For example, imaging device 4 may be a capsule or other unit where all the components including for example power components are substantially contained within a container or shell, and where imaging device 4 does not require any wires or cables to, for example, receive power or transmit information. Imaging device 4 may communicate with an external receiving and display system to provide display of data, control, or other functions. For example, in an autonomous system power may be provided by an internal battery or a wireless receiving system. Other embodiments may have other configurations and capabilities. For example, components may be distributed over multiple sites or units. Control information may be received from an external source.

A non-exhaustive list of examples of body lumens includes the gastrointestinal (GI) tract, a blood vessel, a reproductive tract, or any other suitable body lumen.

Reference is now made to FIG. 2, which is a schematic illustration showing mounts 62 and 64, bases 36 and 38, and circuit board 30 in its spread out form, for example, before being inserted into imaging device 4, according to an embodiment of the invention. Imaging device 4 may be assembled or manufactured, for example, by aligning mounts 62 and 64, bases 36 and 38 of lens holders 54 and 56, circuit board 30, and/or other components or structural mating elements of imaging device 4, and attaching connecting elements, such as, conductive material 22, connector pins 24, and/or contact clips 52, described in greater detail below in reference to FIG. 3. Prior to assembly, contact clips 52 may have a flat, curved, bent, or other suitable shape. Contact clips 52 may be attached, for example, by pressing, bending, soldering, or shaping to fit or hold the assembled components.

In one embodiment, mounts 62 and 64 may include circuit boards 66 and 68, and illumination sources 32 and 34, respectively. For example, each illumination sources 32 and 34 may including at least one LED. Circuit boards 66 and 68 may be in electrical communication with illumination sources 32 and 34 for conveying power for producing light. Examples of methods for illumination sources and mounts therefore, that may be used with embodiments of the present invention are described in, for example, US Publication Number US/2006/0015013 A1 to Gilad et al., which is assigned to the common assignee of the present invention and which is incorporated herein by reference.

According to some embodiments of the present invention, contact clips 52 may secure mounts 62 and 64 to circuit board 30. According to some embodiments, contact clips 52 may be used for providing electrical communication therebetween. For example, contact clips 52 may secure circuit boards 66 and 68 of mounts 62 and 64, to portions 40 and 42 of circuit board 30, respectively. Other configurations or assemblies may be used.

According to some embodiments of the present invention bases 36 and 38 may hold, enclose, or provide structural support for optical systems 50 and 70 and components thereof. For example, bases 36 and 38 may be connected to, or components of, lens holders 54 and 56, respectively. In some embodiments, bases 36 and 38 may be positioned between mounts 62 and 64 and portions 40 and 42 of circuit board 30, respectively. Thus, contact clips 52, which secure mounts 62 and 64 to circuit board 30, may also secure lens holders 54 and 56 to circuit board 30, for providing structural support therebetween.

In one embodiment, circuit board 30 may include one or more (e.g., two) wider portions 40 and 42, connected to one another by means of a narrower portion 44. In some embodiments, portions 40, 42, and/or 44 may include distinct circuit boards or may be part of one continuous circuit board. Portions 40, 42, and 44 may include flexible, moveable, jointed, and/or rigid circuit board material. In embodiments where wider portions 40 and 42 include flexible circuit board material, there may be attached underneath rigid portions (not shown) enabling, for example, the structural stability of the components mounted on portions 40 and 42.

According to one embodiment components of imaging device 4, for example, transmitter 18, control block 20, optical systems 50 and 70 and/or illumination sources 32 and 34, may be mounted or disposed upon portions 40 and 42. In some embodiments, such components may be folded as necessary. Circuit board 30 may include one or more power source contacts, for example, connecting circuit board 30 to power source 16, for example, a battery.

In one embodiment, optical systems 50 and 70 may be mounted separately on opposite ends of circuit board 30, for example, on portions 40 and 42, respectively. Illuminations mounts 62 and 64 may be arranged in any desirable configuration, for example, to include illumination sources 32 and 34 positioned along ring shaped circuit boards 66 and 68, and centered about optical imagers 60 and 58, respectively. According to embodiments of the present invention, components may be assembled in a variety of configurations to create a variety of shaped and sized imaging devices 4.

Figure 3:
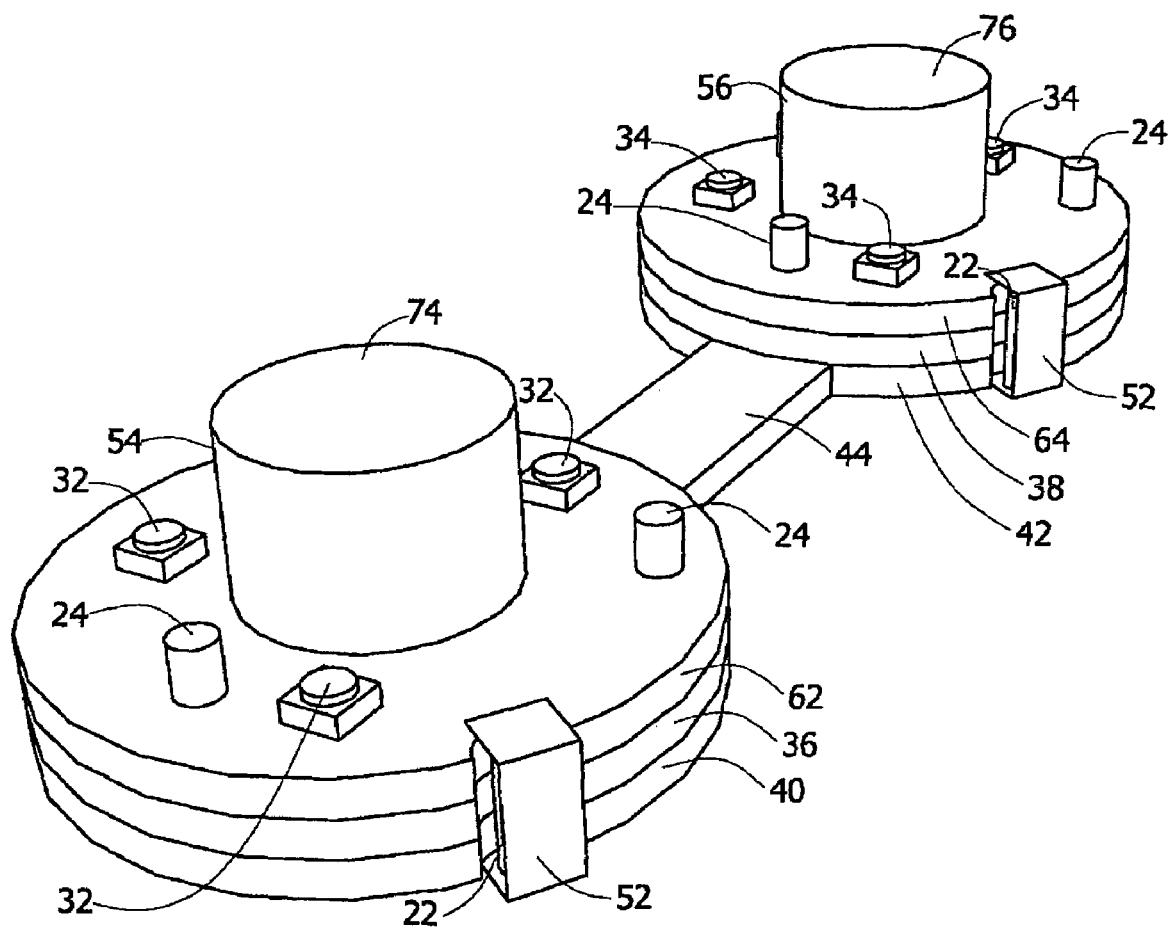
FIG. 3 is a schematic illustration showing mounts mounted on a circuit board using contact clips, according to an embodiment of the invention.

Reference is now made to FIG. 3, which is a schematic illustration showing mounts 62 and 64 mounted on circuit board 30 using contact clips 52, according to an embodiment of the invention. Mounts 62 and 64 may include or may be in electrical communication with one or more illumination sources 32 and 34, respectively, including, for example, one or more LEDs.

Contact clips 52 may secure mounts 62 and/or 64 to circuit board 30, for example, to portions 40 and 42, respectively. Thus, contact clips 52 may provide electrical communication between circuit board 30 and mounts 62 and/or 64. For example, contact clips 52 may include conductive material for transporting the power supplied by power source 16 to illumination sources 32 and/or 34 and/or other components in electrical communication with mounts 62 and/or 64. In some embodiments, contact clips 52 may be insulated, for example, with a protective layer. In some embodiments, contact clips 52 may be formed from a solid conductive material, for example, a copper clamp. In other embodiments, contact clips 52 may be formed of a plurality of parts, for example, a series of conductive wires, such as copper wires, encased in a solid plastic housing. Other materials or shapes may be used.

In some embodiments, other connecting element may be used, for example, in addition to, or instead of, contact clips 52. In some embodiments, connector pins 24 may be used for orientating mounts 62 and 64, bases 36 and 38, and/or circuit board 30. For example, connector pins 24 may be mating elements, protruding from circuit board 30. The positioning of grooves 26 and 28, recessed for mating with connector pins 24, may provide an alignment for assembling mounts 62 and 64 to bases 36 and 38, and/or circuit board 30. In other embodiments, connector pins 24 may be used for providing electrical communication between mounts 62 and 64 and circuit board 30. In one embodiment, for example, one connector pin 24 may be used for orientating while another connector pin 24 may be used for providing electrical communication. In one embodiment, at least a portion of contact clip 52 may be soldered to mounts 62 and/or 64, bases 36 and/or 38, and/or circuit board 30 using conductive material 22. Alternately, both ends of contact clip 52 may be soldered to their respective contacts. The positioning of grooves 27 and 29, recessed for mating with conductive material 22, may provide an alignment for assembling mounts 62 and 64 to bases 36 and 38, and/or circuit board 30. Connector pins 24 and conductive material 22 may be sufficiently conductive to transport power supplied by power source 16 to illuminate illumination sources 32 and/or 34 and/or other components in electrical communication with mounts 62 and/or 64. In some embodiments, such connections may be formed using only one of contact clips 52, conductive material 22, and connector pins 24. In other embodiments, a combination of contact clips 52, additional conductive material 22, and connector pins 24 may be used.

In some embodiments, mounts 62 and 64, and/or bases 36 and 38 may have surfaces designed to fit against a surface of circuit board 30. For example, mounts 62 and 64 and/or bases 36 and 38 may include grooves 26 and/or 27 and 28 and/or 29, respectively, into which connector pins 24 and conductive material 22 are configured to fit. Mounts 62 and 64 and/or bases 36 and 38 may include clamps or screws to form secure connections with circuit board 30. Projections, such as connector pins 24 and conductive material 22, and recesses such as grooves 26, 27, 28, and 29 and other equivalent structural mating elements may provide alignment and structural support for fitting circuit board 30, bases 36 and 38, and/or mounts 62 and 64. Any combination of grooves 26, 27, 28, and 29 may be used. Other materials or types of connections may be used.

Figure 4:
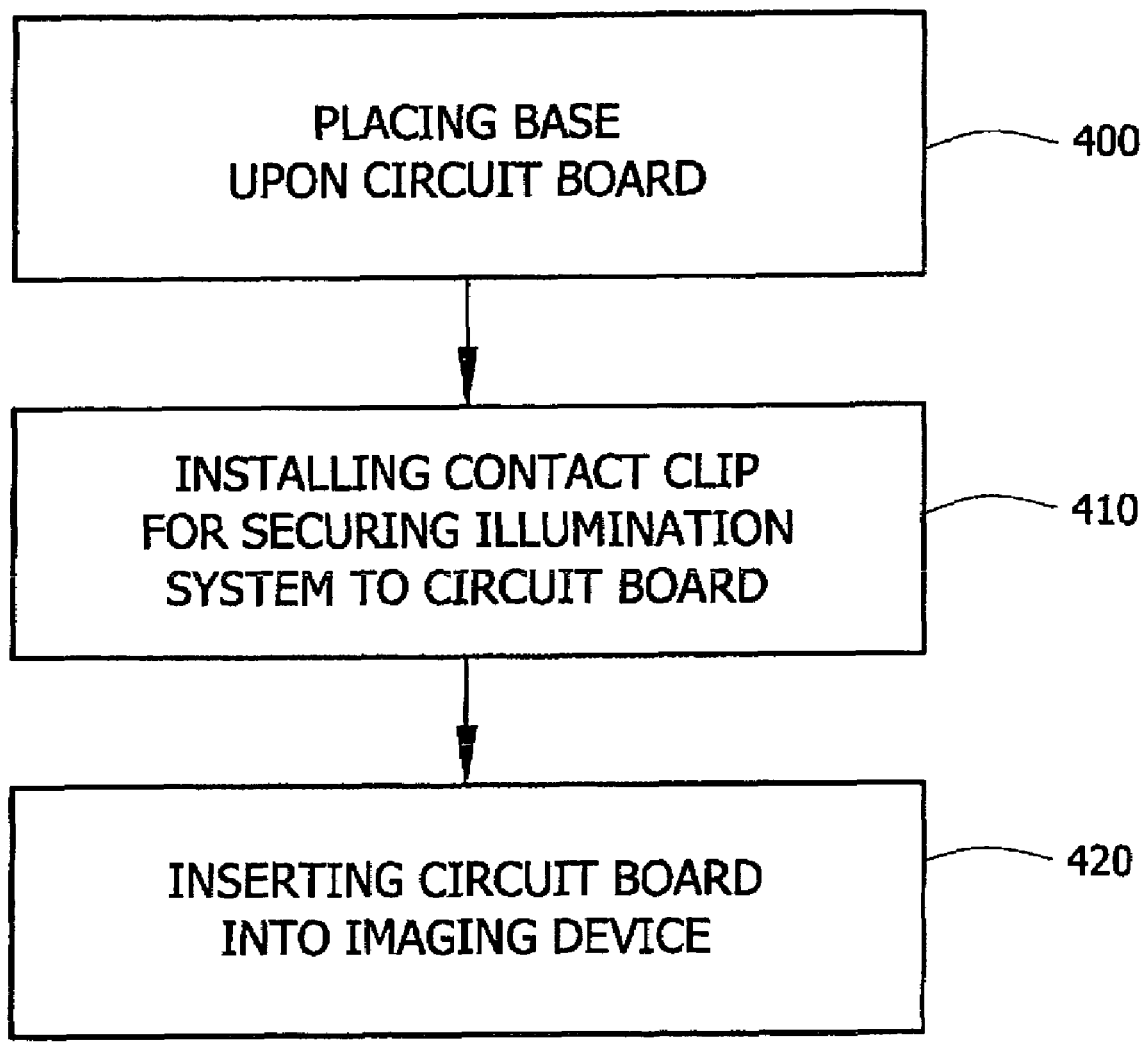
FIG. 4 is a flowchart depicting a method for producing an in vivo device which includes a mount, a circuit board, and contact clips according to embodiments of the invention.

Reference is now made to FIG. 4, which is a flowchart depicting a method for producing an in vivo device (e.g., imaging device 4) which includes mounts (e.g., mounts 62 and/or 64), a circuit board (e.g., circuit board 30), bases (e.g., bases 36 and/or 38), and contact clips (e.g., contact clips 52) according to embodiments of the invention.

In operation 400 various components of the imaging device, including one or more mounts, which may each have, or may be in electrical communication with, at least one LED, may be placed on a circuit board. Additional components may be placed on the circuit board. For example, power source 16, transmitter 18, control block 20, optical systems 50 and 70 and/or illumination sources 32 and 34 may be disposes on portions 40 and/or 42 of the circuit board (as was described with reference to FIG. 2). Other specific components may be used. In some embodiments, a surface of the circuit board may be designed to fit such components.

In operation 410 the contact clip may be installed to secure one or more of the mounts to the circuit board and/or for providing electrical communication therebetween. Other connections, for example, connections using conductive materials, such as solder, or connection pins, may be used in addition to, or instead of, contact clips, according to embodiments of the invention. For example, the contact clip may be soldered to one or more mounts and/or to the circuit board.

In operation 420 the circuit board may be inserted into the in vivo imaging device, for example, into a device housing. Operation 420 may include, for example, folding portions of the circuit board (e.g., portions 40 and 42) along flexible, moveable or jointed portions, (e.g., portion 44), so that the circuit board fits into the device housing. The circuit board may be capable of folding according to several designs, enabling the circuit board to fit into devices of different shapes and/or sizes.

Examples of methods for folding circuit boards that may be used with embodiments of the present invention are described in, for example, US Publication Number US/2006/0044614 A1 to Cohen, US Publication Number US/2006/0004257 A1 to Gilad et al., and US Publication Number US/2004/0171914 A1 to Avni, each of which is assigned to the common assignee of the present invention and which is incorporated by reference.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A method of manufacturing an in vivo imaging device, comprising:
   a) providing a mount having at least one illumination source, wherein said mount is in electrical communication with said illumination source;
   b) placing said mount upon a flexible circuit board;
   c) installing a contact clip for securing said mount to said circuit board and for providing electrical communication therebetween; and
   d) folding said circuit board.

2. The method of claim 1, further comprising soldering said contact clip to said mount.

3. The method of claim 1, further comprising soldering said contact clip to said circuit board.

4. The method of claim 1, further comprising providing electrical communication between said contact clip and a power source.

5. The method of claim 1, further comprising positioning a base housing a lens between said mount and said circuit board.

6. The method of claim 1, further comprising inserting said circuit board into said in-vivo imaging device.

* * * * *